United States Patent
Eversdijk

(10) Patent No.: US 7,452,714 B2
(45) Date of Patent: Nov. 18, 2008

(54) DEVICE AND METHOD FOR STORAGE AND TRANSPORTATION OF FORENSIC AND/OR BIOLOGICAL MATERIAL

(76) Inventor: Martin Jan Peter Eversdijk, Flierveld 59, Nieuw Vennep (NL)

( * ) Notice: Subject to any disclaimer, the term of this patent is extended or adjusted under 35 U.S.C. 154(b) by 82 days.

(21) Appl. No.: 10/545,499

(22) PCT Filed: Feb. 16, 2004

(86) PCT No.: PCT/NL2004/000114

§ 371 (c)(1),
(2), (4) Date: Aug. 12, 2005

(87) PCT Pub. No.: WO2004/071305

PCT Pub. Date: Aug. 26, 2004

(65) Prior Publication Data

US 2006/0078988 A1    Apr. 13, 2006

(30) Foreign Application Priority Data

Feb. 14, 2003   (NL) .................................... 1022680

(51) Int. Cl.
*C12M 1/26* (2006.01)
*A61B 10/02* (2006.01)
*A61M 35/00* (2006.01)
*G01N 1/00* (2006.01)

(52) U.S. Cl. .................... 435/309.1; 422/100; 422/102; 73/864.72; 600/572; 604/1; 15/184; 15/209.1; 15/244.1; 206/361

(58) Field of Classification Search ............... 435/309.1; 73/864.72; 600/572; 604/1; 15/208, 209.1, 15/210.1, 244.1, 184; 206/361
See application file for complete search history.

(56) References Cited

U.S. PATENT DOCUMENTS

| | | | | |
|---|---|---|---|---|
| 2,527,741 A | * | 10/1950 | Lamonde | 222/103 |
| 2,584,042 A | * | 1/1952 | Ober | 206/209.1 |
| 2,677,842 A | * | 5/1954 | Sherwin | 15/210.1 |
| 2,719,315 A | * | 10/1955 | Sheehan | 15/210.1 |
| 2,736,917 A | * | 3/1956 | Goldstein et al. | 15/104.94 |
| 3,004,681 A | * | 10/1961 | Jinkens et al. | 215/227 |
| 3,321,796 A | * | 5/1967 | Lelicoff | 15/104.94 |
| 4,527,574 A | * | 7/1985 | Manfredi | 132/308 |
| 4,753,349 A | | 6/1988 | Monek | |

(Continued)

FOREIGN PATENT DOCUMENTS

EP    0 101 981 A2    3/1984

(Continued)

OTHER PUBLICATIONS

International Search Report dated Jun. 9, 2004, of corresponding PCT/NL2004/000114.

(Continued)

*Primary Examiner*—William H Beisner
(74) *Attorney, Agent, or Firm*—Christie, Parker & Hale, LLP

(57) ABSTRACT

A device for storage and transportation of forensic and/or biological material, comprising a sealable container and a material holder for holding the material, which holder can be placed in the container, wherein the container is provided with at least one ventilating hole and with sealing means that shut off the interior of the container from the environment.

14 Claims, 1 Drawing Sheet

Figure 1:
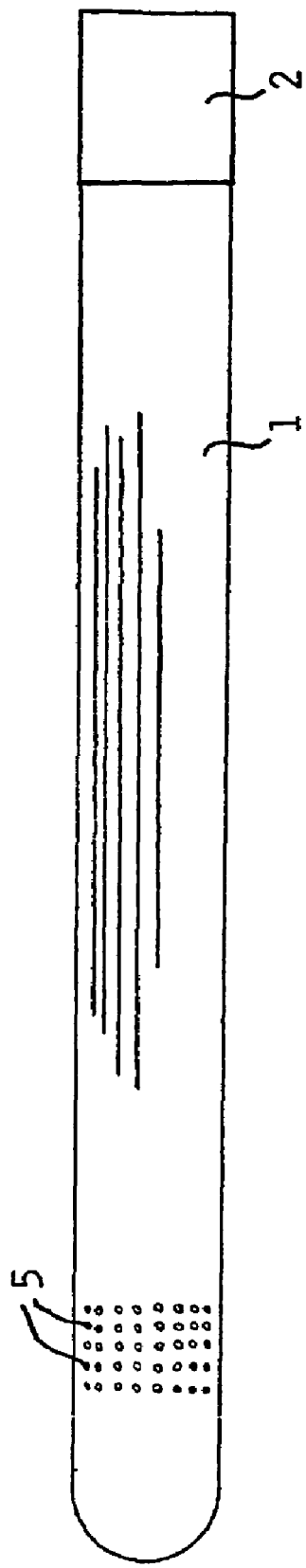

U.S. PATENT DOCUMENTS 5,000,193 A * 3/1991 Heelis et al. ................ 600/573
5,832,940 A * 11/1998 Embry et al. ................ 132/309
5,874,045 A    2/1999 Chisum
6,312,395 B1  11/2001 Tripp et al.

FOREIGN PATENT DOCUMENTS

EP    0 101 982 A2    3/1984
GB    2189398 A *    10/1987

OTHER PUBLICATIONS

Written Opinion of the International Searching Authority of corresponding PCT/NL2004/000114, no date provided.

* cited by examiner

DEVICE AND METHOD FOR STORAGE AND TRANSPORTATION OF FORENSIC AND/OR BIOLOGICAL MATERIAL

CROSS-REFERENCE TO RELATED APPLICATION

This application is a National Phase Patent Application of International Application Number PCT/NL2004/000114, filed on Feb. 16, 2004, which claims priority of Netherlands Patent Application Number 1022680, filed on Feb. 14, 2003.

The invention relates to a device for storage and transportation of forensic and/or biological material, comprising a sealable container and a material holder for holding the material, which holder can be placed in the container.

Such a device is known. The known device is used inter alia in the case of criminal offences for taking a sample of possible perpetrator traces at the site where the criminal offense has been committed. This is done by removing the material holder, which comprises a cotton swab, from the sterile container, taking the sample therewith and subsequently placing it back in the tubular container. The cotton swab is mounted in a cap, which seals the container hermetically. The sealed container is then transported to a laboratory, where the sample is examined, for example for the presence of DNA material of a possible perpetrator. If the sample contains moisture, for example blood or another bodily fluid, the sample needs to be dried as quickly as possible by removing the cap with the cotton swab from the container and allowing it to dry in the air in an at least substantially sterile environment, because biological decomposition processes may take place in the moist environment of the container, which processes may lead to the DNA material being destroyed. It is important that said drying of the sample takes place in a substantially sterile environment, because contamination with foreign material must be prevented.

The operations of removing the cotton swab from the container, allowing the material to dry, and placing it back in the container take a lot of time, requiring a special, conditioned space, and involves the risk of mistakes being made, since great care must be taken in placing back the material in the container, because the sample must not be placed in the wrong container, of course.

The object of the invention is to provide a device of the above kind which is easier to work with, which requires fewer external provisions and/or which reduces the risk of mistakes being made.

In order to accomplish that object, the container is provided with at least one ventilating hole and with sealing means that shut off the interior of the container from the environment. In a first preferred embodiment, the sealing means comprise a removable seal that seals the ventilating hole. The term seal is understood to include any sealing material that can be removed, at least be taken off or out of the ventilating hole, thus releasing the ventilating hole. In a second preferred embodiment, the sealing means comprise a removable envelope, for example a blister pack, in which the container is packaged as a whole.

In this way it is possible, once the forensic material has been placed in the container, to allow the material to dry in the air whilst remaining inside the container. Since this reduces the risk of contamination with foreign DNA material from the environment, less stringent requirements need to be made with regard to the sterility of the environment.

In a first preferred embodiment, the ventilating hole is formed in the cap. In the second preferred embodiment, the ventilating hole is formed in the wall of the container, preferably near the location where the forensic material is kept in the container. Preferably, the container is provided with several ventilating holes having a diameter of less than 1 mm. The use of a multitude of small holes reduces the risk of contamination from the environment in comparison with the situation in which one larger hole is used.

Usually, the container has a length of 10-23 centimeters, preferably 15-18 centimeters, and the container preferably has a diameter of 8-20 mm, preferably 10-15 mm. In many cases the container is substantially made of a transparent plastic, so that a visual inspection of the contents is possible without opening the container.

The invention also relates to a method for storage and transportation of forensic and/or biological material, wherein a material holder is used for holding the material, and wherein the material holder is placed in a sealable container, wherein the container is provided with at least one ventilating hole upon placement of the material holder. To that end, a seal that covers previously formed ventilating holes may be removed, for example.

Figure 2:
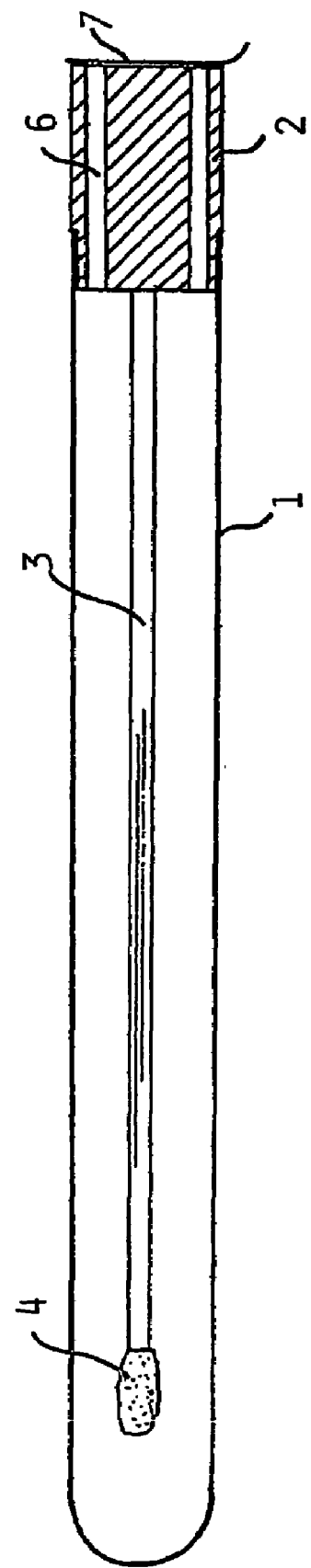

The invention will now be explained in more detail in by means of embodiments as shown in the figures, in which:

FIG. 1 is a view of a first embodiment of a device according to the invention; and FIG. 2 is a sectional view of a second embodiment of a device according to the invention.

The two devices for storage and transportation of forensic material that are shown in FIG. 1 and FIG. 2 comprise a tubular container 1, which is made of a transparent plastic material, and a cap 2, which is in principle capable of sealing the container 1 hermetically at one end. A cotton swab 3 is provided in the cap 2 in both embodiments, which cotton swab is only shown in the sectional view of FIG. 2, however. A wad of cotton wool 4 is present at the end of the cotton swab 3.

According to FIG. 1, the container is provided with a multitude of the ventilating holes 5, which are located approximately at the level of the wad of cotton wool 4. In unused condition, the contents of the container are sterile and the holes 5 are covered and sealed by a seal (not shown).

According to FIG. 2, the container 1 itself is not provided with ventilating holes, but continuous ventilating channels 6 are present in the cap 2. Said ventilating channels 6 are covered and sealed by a seal 7, which can easily be removed.

Instead of using a seal 7 at the location of the ventilating holes, it is also possible to use an enveloping package in which the container 1 is packaged as a whole.

In use, for example at the site where a criminal offense has been committed, the seal or the package can easily be removed, and the cap 2 with the cotton swab 3 and the wad of cotton wool 4 is removed from the container for taking a sample of DNA material, paint residue, fibres or the like, after which it is placed back in the container 1. Any moisture contained in the sample that has been taken can subsequently evaporate and exit the container via the ventilating holes 5 or the ventilating channels 6.

The invention claimed is:

1. A device for storage and transportation of forensic and/or biological material, comprising a sealable container and a removable sealing cap, wherein a swab provided at one outer end portion with a wad for holding the material is fixed to the sealing cap at its other outer end portion such that the swab with the wad extends in the container, wherein the wad surrounds said end portion of the swab, wherein the container is provided with at least one ventilating hole formed in a wall of the container approximately at a level of the wad and with removable sealing means for shutting off the interior of the container from an external environment.

2. A device according to claim 1, wherein the removable sealing means comprises a removable seal that seals the ventilating hole.

3. A device according to claim 1, wherein the removable sealing means comprises a removable envelope, in which the container is packaged as a whole.

4. A device according to claim 1, wherein the container is provided with several ventilating holes having a diameter of less than 1 mm.

5. A device according to claim 1, wherein the wad is a cotton wad.

6. A device according to claim 1, wherein the container has a length in a range of 10-23 centimeters.

7. A device according to claim 1, wherein the container has a diameter in a range of 8-20 mm.

8. A device according to claim 1, wherein the container is substantially made of a transparent plastic material.

9. A device according to claim 1 wherein the wad covers an entire tip of said swab.

10. A device according to claim 1 wherein the container is tubular.

11. A device as recited in claim 1 wherein the container has a length in a range of 15 to 18 centimeters.

12. A device as recited in claim 1 wherein the container has a diameter in a range of 10 to 15 mm.

13. A device for storage and transportation of forensic and/or biological material, comprising:
    a sealable container;
    a removable sealing cap sealing an end of said container;
    a swab comprising a tip at a first end and a second end opposite the first end, wherein the second end is retained by the sealing cap;
    a wad covering said entire tip for holding the material, wherein said wad extends within said container, wherein said container comprises at least one ventilating hole formed in a wall of the container approximately at a level of the wad; and
    removable sealing means for covering said at least one ventilating hole.

14. A device as recited in claim 13 wherein said wad surrounds an end portion of said swab.

* * * * *